United States Patent [19]

Gibson

[11] Patent Number: 4,975,441

[45] Date of Patent: Dec. 4, 1990

[54] LACTAMS, THEIR SYNTHESIS AND USE IN COSMETIC COMPOSITIONS

[75] Inventor: Walter T. Gibson, Northants, United Kingdom

[73] Assignee: Unilever Patent Holdings B.V., Rotterdam, Netherlands

[21] Appl. No.: 326,954

[22] Filed: Mar. 22, 1989

[51] Int. Cl.$^5$ ............... A61K 31/445; C07D 211/76
[52] U.S. Cl. .................... 514/328; 514/183; 514/210; 514/212; 514/423; 514/425; 540/526; 540/463; 540/354; 546/113; 546/116; 546/223; 548/544
[58] Field of Search ............ 540/526, 463, 354; 546/113, 116, 223; 548/544; 514/328, 425, 423, 212, 210, 183

[56] References Cited

U.S. PATENT DOCUMENTS 4,139,619  2/1979  Chidsey, III ............... 424/45

FOREIGN PATENT DOCUMENTS

| 35919 | 9/1980 | European Pat. Off. | 514/460 |
| 74191 | 3/1983 | European Pat. Off. | 546/223 |
| 2357069 | 6/1973 | Fed. Rep. of Germany | 546/223 |
| 59-186911 | 10/1984 | Japan | 514/460 |
| 1440670 | 6/1976 | United Kingdom | 546/223 |
| 1577868 | 10/1980 | United Kingdom | 546/223 |
| 8504577 | 10/1985 | World Int. Prop. O. | 546/116 |

OTHER PUBLICATIONS

"Bulletin of the Chemical Society of Japan", vol. 51, No. 11, Nov. 1978, pp. 3261-3266, M. Kinoshita, Synthetic Approach to 2,3,5-Triamino-2,3,5-Trideoxy-D-Arabonic Acid Derivatives from 3,4,6-Triazido-3,4,6-Trideoxy-1,2,0-Isopropylidene-α-D-Glucopyranose.
"Chemical Abstracts", vol. 109, No. 25, Dec. 1988, p. 363, Abstract No. 225518u, Columbus, Ohio, U.S.; M. Yukio et al., Inhibition of β-Galactosidase by Galactostatin, Galactostatin Lactam, and 1-Deoxygalactostatin.
"Agric. Biol. Chem.", 1988, 52(7), 1649-1654.
Brimacombe et al., "Carbohyd. Res.", 8, 82-88 (1968).
Gramera et al., "J. Org. Chem.", 28 (63), 1401.
Whistler and Lake, "Methods in Carbohyd. Chem.", 6, 286-291 (1972).
Jacquinet et al., "Carbohyd. Res.", 130, 221-241 (1984).
Meyer et al. (1961), "Proceedings of the Society of Experimental and Biological Medicine", 108, 59-61.
Oliver, R. F. (1970), "J. Embryol. Exp. Morphol.", 23, 219-236.
Couchman, J. R. and Gibson, W. T. (1985), "Dev. Biol.", 108, 290-298.
Montagna W. et al. (1952), "Q. J. Microsc. Sci.", 93, 241-245.
"Journal of Organic Chemistry", vol. 34, No. 3, Mar. 1969, pp. 675-681, S. Hanessian, Sugar Lactams, III, Synthesis of Five-Six-, and Seven-Memered Analogs 1-3.
"Journal of Antibiotics", vol. 37, No. 12, 1984, pp. 1579-1583, T. Niwa et al., Novel Glycosidase Inhibitors, Nojirimycin B and D-Mannonic-Delta-Lactam, Isolation, Structure Determination and Biological Property.
"Journal of the Chemical Society", No. 7, 1988, pp. 483-485, Copyright the Royal Society of Chemistry, G. W. J. Fleet, δ-Lactams: Synthesis from D-Glucose, and Preliminary Evaluation as a Fucosidase Inhibitor, of L-Fuconic-δ-Lactam.

Primary Examiner—Robert T. Bond
Attorney, Agent, or Firm—Milton L. Honig

[57] ABSTRACT

A composition suitable for topical application to mammalian skin or hair for inducing, maintaining or increasing hair growth comprises:
(i) a chemical inhibitor of glycosidase activity chosen from lactams having the structure:

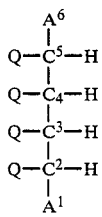

(1)

where $A^1$ and $A^6$ are —H, —CH$_3$,

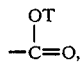

—CH$_2$OT or

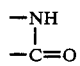

$A^1$ and $A^6$ being the same or different, and at least one of which being the group:

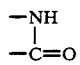

in a lactam ring;
and where Q is —OT', —NHT' or a lactam linkage to $A^1$ or $A^6$;
the Q groups being the same or different, and at least one of which is involved in a lactam linkage;
and where T is the same or different and is chosen from —H, —C$_p$H$_{2p+1}$ or a metal ion,
T' is —H or —COC$_p$H$_{2p+1}$, and
p is an integer of from 1 to 22;
provided that:
where any of the Q groups is —OT' or —NHT', then that group or groups can be of either stereochemical configuration with respect to the plane of the ring; and
(ii) a cosmetically acceptable vehicle for the chemical inhibitor.

Certain novel lactams are also claimed.

19 Claims, No Drawings

LACTAMS, THEIR SYNTHESIS AND USE IN COSMETIC COMPOSITIONS

FIELD OF THE INVENTION

The invention relates to novel lactams, particularly those having from 3 to 5 carbon atoms in the lactam ring, and to their synthesis. The invention also relates to the use of the novel lactams, and to certain known lactams in cosmetic or pharmaceutical compositions intended for topical application to skin or hair in order to promote hair growth.

PRIOR ART

D-glucaro-1,5-lactam is identified by Meiji Seika Kaisha Ltd in GB No. 1 577 868 and certain alkyl esters thereof in GB No. 1 440 670 by the same patentee.

DEFINITION OF THE INVENTION: COMPOUND PER SE

The novel lactams of the invention have the structure:

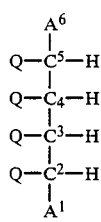
(1)

where $A^1$ and $A^6$ are —H, —CH$_3$,

,

—C$_2$OT or

, $A^1$ and $A^6$ being the same or different, and at least one of which being the group:

in a lactam ring;
and where Q is —OT′, —NHT′ or a lactam linkage to $A^1$ or $A^6$;
the Q groups being the same or different, and at least one of which is involved in a lactam linkage;
and where T is the same or different and is chosen from —H, —C$_p$H$_{2p+1}$ or a metal ion,
T′ is —H or —COC$_p$H$_{2p+1}$, and
p is an integer of from 1 to 22;
provided that:
where any of the Q groups is —OT′ or —NHCOT′, then that group or groups can be of either stereochemical configuration with respect to the plane of the ring.
provided also that where the lactam has the structure:

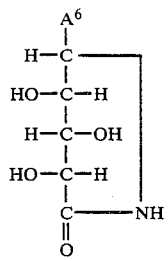
(1a)

and when $A^6$ is

and T is —C$_p$H$_{2p+1}$, then p is an integer of from 5 to 22.

Particular examples of novel lactams according to the invention include the following:

L-Galactono-1,4-lactam, having the structure (3)

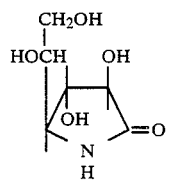
(3)

L-Arabino-1,5-lactam, having this structure (4)

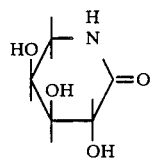
(4)

D-Fucono-1,5-lactam, having the structure (5)

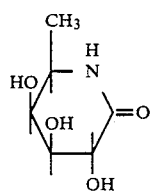
(5)

D-Glucaro-1,4-lactam, having the structure (6):

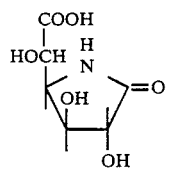
(6)

D-Glucurono-6,3-lactam, having the structure (7):

1,2,5-tri-O-acetyl-D-glucurono-6,3-lactam having the structure (8):

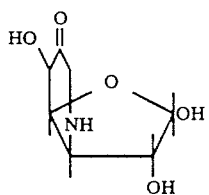

2-Acetamido-2-deoxyglucono-1,5-lactam, having the structure (9):

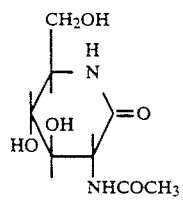

2-Acetamido-2-deoxygalactono-1,5-lactam, having the structure (10):

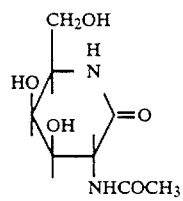

D-Glucaro-1,4:6,3-dilactam, having the structure (11):

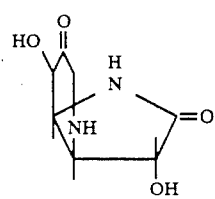

L-Idaro-1,5-lactam, as having the structure (12):

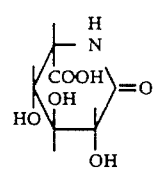

Particular examples of esterified forms of aldarolactams include the following:

2,3,5-Tri-O-acetyl-D-glucaro-1,4-lactam, having the structure (13):

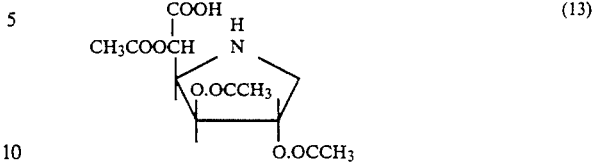

2,5-Di-O-acetyl-D-Glucaro-1,4:6,3-dilactam, having the structure (14):

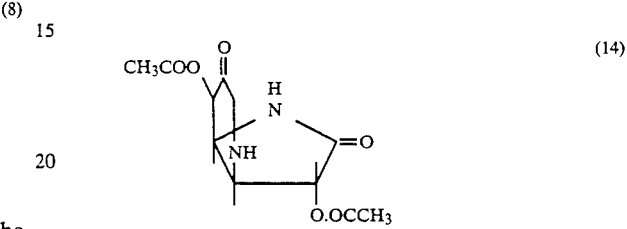

L-Idaro-1,5-lactam methyl ester, having the structure (15):

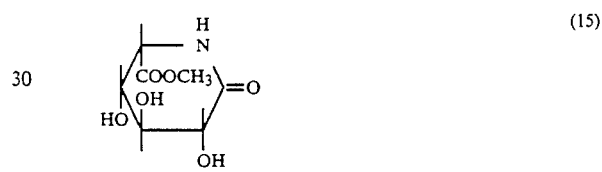

2-Propionoamide-2-deoxyglucaro-1,5-lactam, having the structure (16):

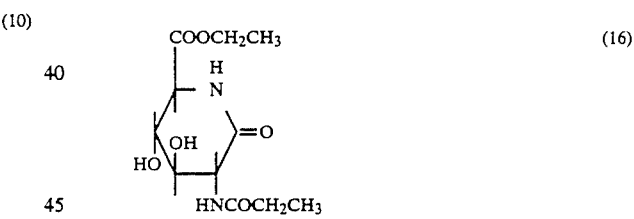

SYNTHESIS OF THE NOVEL LACTAMS

Certain of the novel 1,5 lactams according to the invention (e.g. structure 18 below) can be prepared from an esterified deoxyamino uronic acid (for example, structure 17), by treatment with a base:

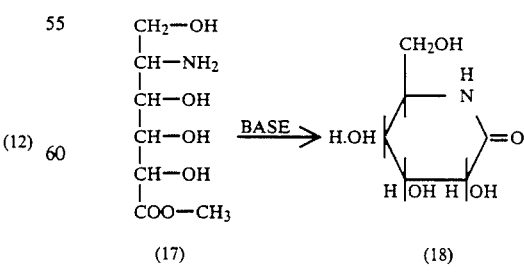

Another method suitable for the synthesis of 1,5 lactams according to the invention involves catalytic reduction of a 5-azido1,4-lactone (19):

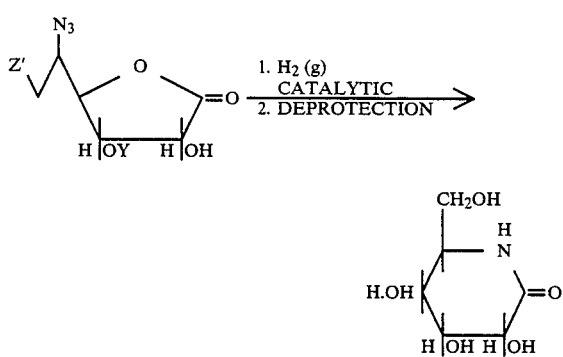

where Y and Z' are suitable protecting groups, for example trityl or benzyl. In the special case where C-6 is COOR (where R is alkyl), then the above route yields aldarolactone (see pathway for structure (12)).

Aldarolactams (20) may also be prepared from the corresponding aldonolactams (18) by catalytic oxidation reactions

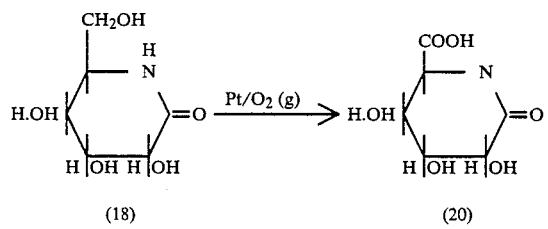

Synthesis of L-idaro-1,5-lactam (structure 12)

By way of example, the synthesis of a novel lactam according to the invention will now be described.

The synthesis of L-idaro-1,5-lactam (12) involves a multi-stage synthesis starting from 1,2:5,6-di-D-glucofuranose (A). All reactions were followed by thin layer chromatography and structural confirmation of the intermediates was performed using proton and C-13 NMR, IR and in some cases optical rotation values.

3-O-Benzyl 1,2:5,6-di-O-isopropylidene-α-D-glucofuranose (B) was prepared by the reaction of (A) with benzyl bromide and sodium hydride in N,N-dimethyl-formamide (DMF) as described by Brimacombe et al., [Carbohyd. Res. 8, 82–88 (1968)].

(B) was obtained as an oil in 95% yield ($[\alpha]_D^{25} -26.2°$ in ethanol).

Selective deprotection of the 5,6-isopropylidene group to give (C) was achieved by dissolving crude (B) in 75% aqueous acetic acid and stirring overnight at room temperature, also as described by Brimacombe et al. This gave (C) as an oil (95%, $[\alpha]_D^{25} -48.4°$, C 2.50 (CHCl$_3$)).

Tritylation of the primary hydroxyl group at position 6 was done by reacting (C) with triphenyl methyl chloride in dried pyridine as described by Gramera et al [J. Org. Chem. 28 (63) 1401]. This gave (D) as an oil which was purified by flash chromatography (petroleum ether (40/60): ethyl acetate 10:1 v/v) (95%, $[\alpha]_D^{25} -36.0°$, C 2.97 (CHCl$_3$)).

The 5-O-acetate (E) was prepared according to Whistler and Lake [Methods in Carbohyd. Chem., 6, 286–291 (1972)] by reacting (D) with acetic anhydride and dry pyridine at 0° C. (E) was obtained as a syrup (80%). Preparation of (F) was achieved in three steps as described by Jacquinet et al. [Carbohyd. Res. 130, 221–241 (1984)]. (F) was obtained as an amorphous solid (45%).

The 5-triflate (G) was prepared by reacting (F) with trifluoromethane sulphonic anhydride under anhydrous conditions. This was followed by reacting the crude triflate (G) with sodium azide in DMF at ~50° C. to give the inverted 5-azido-β-L-idofuranuronate (H). (H) was subsequently hydrolysed (50% trifluoroacetic acid (aq.)) to give the diol (I). Selective oxidation at the anomeric hydroxyl was carried out using bromine in aqueous media. This reaction generated the 5-azido-idaro lactone (J). Under conditions of catalytic hydrogenation in the presence of 5–10% Pd/C, (J) gave the methyl ester of L-idaro-1,5-lactam (15), which was subjected to base hydrolysis to give the desired compound (12).

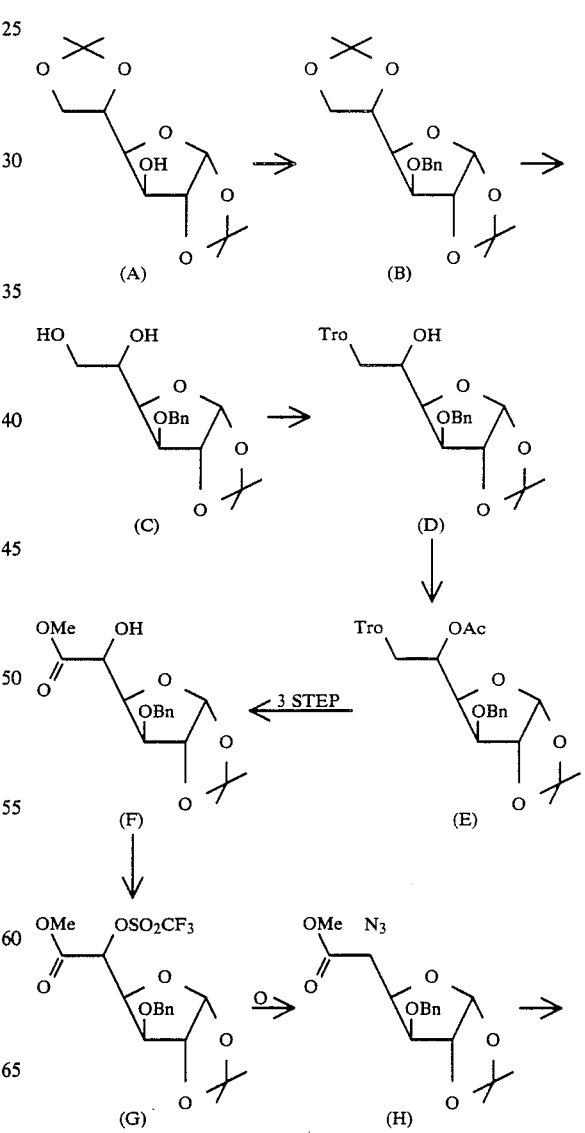

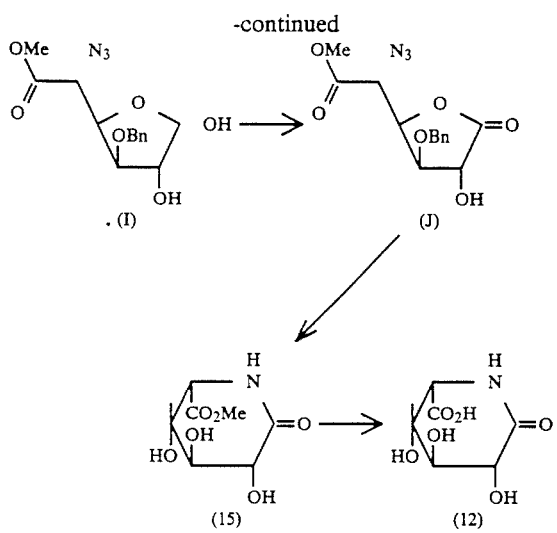

USE OF NOVEL LACTAMS AND CERTAIN RELATED KNOWN LACTAMS IN COSMETIC OR PHARMACEUTICAL COMPOSITIONS INTENDED FOR TOPICAL APPLICATION TO SKIN OR HAIR

FIELD OF THE INVENTION

The invention also relates to cosmetic and pharmaceutical compositions for topical application to mammalian skin or hair, containing certain lactams as enzyme inhibitors which are capable of promoting hair growth, especially terminal hair growth on the human scalp.

BACKGROUND

The Hair Growth Cycle

It should be explained that in most mammals, hair does not grow continuously, but undergoes a cycle of activity involving alternate periods of growth and rest.

The hair growth cycle can be divided into three main stages, namely:

(i) the growth phase known as anagen, during which the hair follicle penetrates deep into the dermis with the cells of the bulb dividing rapidly and differentiating to form the hair, (ii) the transitional stage known as catagen, which is heralded by the cessation of mitosis, and during which the follicle regresses upwards through the dermis and hair growth ceases, (iii) the resting stage known as telogen, in which the regressed follicle contains a small secondary germ with an underlying ball of tightly packed dermal papilla cells.

The initiation of a new anagen phase is revealed by rapid proliferation in the germ, expansion of the dermal papilla and elaboration of basement membrane components. The hair cycle is then repeated many times until, as a consequence of the onset of male pattern baldness, most of the hair follicles spend an increasing proportion of their time in the telogen stage, and the hairs produced become finer, shorter, and less visible; this is known as terminal to vellus transformation.

PRIOR ART

Alleged Baldness Cures

Although there have been many claims in the scientific literature to the promotion or maintenance of hair growth by the topical application of hair tonics and the like, with the possible exception of minoxidil, none has been shown to be sufficiently free from disadvantageous clinical side effects, whether administered topically, orally or systemically, to warrant commercial exploitation as an ethical pharmaceutical, proprietary medicine, or as a cosmetic product. Possibly, the only means which has met with partial success for growing hair on the bald or balding human head is by transplantation of hair to the bald areas. This is, however, an extremely painful operation and is not always successful. Furthermore, it is immediately apparent to the casual observer that the subject has received a hair transplant and it may take many months or even years before hair regrowth, following this operation, assumes an appearance which resembles that of the original naturally growing hair.

Among the many hair regrowth studies that have been reported in the literature, there is included the work of Bazzano as described in PCT International Publication No. WO 85/04577. This publication describes a composition which is useful for increasing the rates of hair growth on mammalian skin, prolonging the anagen phase of the hair growth cycle and for treating various types of alopecias. The composition in question comprises a pyrimidine carbamate.

It has also been reported in U.S. Pat. No. 4,139,619 to Chidsey assigned to the Upjohn Company, that a topical composition comprising minoxidil as the free base or acid addition salt thereof, or certain specified related iminopyrimidines, is useful in stimulating the conversion of vellus hair to growth as terminal hair, as well as increasing the rate of growth of terminal hair.

In spite of the apparent stimulation of hair growth or regrowth reported independently by Bazzano and Chidsey, following topical application of minoxidil or related compounds, there is general concern that systemic side-effects can result, particularly following topical application of minoxidil. Thus it is generally recognised in the medical literature that the side effects of orally administered minoxidil are very serious, and include fluid retention, tachycardia, dyspnea, gynecomastia, fatigue, nausea and cardiotoxicity.

In addition to the alleged benefits of employing the pyrimidine carbamates of Bazzano or minoxidil of Upjohn, many other hair regrowth studies have been reported in the literature In particular, the work of Meyer et al (1961) in the Proceedings of the Society of Experimental and Biological Medicine, 108, 59–61, is worthy of mention. Meyer and his co-workers repeatedly injected acid mucopolysaccharides into the skin of shaved rabbits and reported observing the initiation of the hair growth cycle with stimulation of hair growth which in some instances appeared to be thicker than usual. They found that heparan sulphate was particularly active, while dermatan sulphate and chondroitin-6-sulphate were also active in this respect, but to a lesser extent.

It has also been reported by Frajdenrajch in EP-A-No. 0 035 919 to include chondroitin sulphate in a hair composition in order to prevent loss and encourage growth of the hair.

Also, Shansho Seigaku in JA-No. 59/186911 describes a shampoo containing a mucopolysaccharide such as chondroitin sulphate.

There are also other references, mainly of Japanese origin, which claim the use of chondroitin sulphate in preparations for topical application to human skin, particularly as hair tonics.

Kohler in DE OLS No. 24 38 534 reports that D-glucuronic acid and glucuronic acid-γ-lactone (also known as glucurono-6,3-lactone) can be applied externally to the skin, together with vitamin C and water, ethanol or aqueous ethanol as a vehicle, as a scalp care agent. In a particular experiment, Kohler reports regrowth of hair following daily application for six months of a 1% solution of D-glucuronic acid.

Kohler et al in DE OLS No. 26 19 100 also claims the use of glucuronic acid or glucuronic acid-γ-lactone as inhibitors in agents for inhibiting the activity of β-glucuronidase, particularly in combination with vitamin $B_{12}$. Whereas Kohler et al. are concerned with β-glucuronidase as found in unusually high concentrations in healing wounds and cancer tissues, they do state that the agents also have a beneficial effect on the loss of hair.

Background to the Invention

The above review of the most relevant references concerning the alleged promotion of hair growth following topical or systemic application of specified molecules, has prompted the study in greater detail, of the biological and biochemical mechanisms involved in the control of the hair growth cycle. The reported role of the dermal papilla which is situated at the base of the hair follicle, and the closely related cells of the connective tissue sheath which surrounds the hair follicle are alleged to be of key importance in governing the cyclic behaviour of hair follicles. This has been shown, for example, directly by Oliver R F (1970) J Embryol Exp Morphol., 23, 219-236, and the changes in the dermal papilla during the hair cycle are consistent with these observations. At the end of anagen, there is a sudden loss of fibronectin [Couchman J R and Gibson W T, (1985) Dev Biol., 108, 290-298] and metachromatic (glycosaminoglycan) staining [Montagna W et al, (1952) Q J Microsc Sci., 93, 241-245] from the connective tissue matrix of the dermal papilla which then undergoes condensation.

Conversely, expansion and elaboration of new matrix is associated with the onset of anagen. A direct role of matrix components in stimulating hair growth was suggested by the work of Meyer et al (1961), [supra].

It is accordingly apparent that glycosaminoglycan breakdown is an important early change in catagen, and since there is already evidence for a link between the presence of intact glycosaminoglycans and hair growth, we have suggested that prevention of glycosaminoglycan breakdown may lead to earlier onset and/or prolongation of anagen. This would effectively retard hair loss and reverse baldness.

One of the more important classes of enzymes that are implicated in the breakdown of glycosaminoglycans are glycosidases. It follows that glycosaminoglycan breakdown may be prevented, inter alia, by inhibiting glycosidase activity.

We have now identified certain lactams as chemical inhibitors of key glycosidases, involved in the breakdown of glycosaminoglycan chains.

It should be explained by "chemical inhibitor" is meant a substance that is physiologically suitable and safe for topical application to human skin, and which is capable of inhibiting glycosidase activity.

One of the preferred lactams, namely D-glucaro-1,5-lactam, when employed together with an aminoglycosidic antibiotic such as Kanamycin, is claimed by Meiji Seika Kaisha Ltd in GB No. 1 577 868 as being useful in protecting against renal failure or insufficiency by oral or parental administration. The same patentee in GB No. 1 440 670 also discloses the alkyl ester of this lactam and its use when administered orally in the treatment of bladder tumours with associated β-glucuronidase activity.

We have surprisingly found that these lactams, when applied topically to skin will stimulate hair growth in view of their ability to inhibit glycosidase activity, as predicted on the basis of the theory outlined above.

DEFINITION OF THE INVENTION

Accordingly, the invention provides a composition suitable for topical application to mammalian skin or hair for inducing, maintaining or increasing hair growth which comprises:

(i) a chemical inhibitor of glycosidase activity chosen from lactams having the structure:

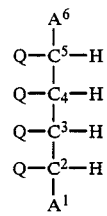   (1)

where $A^1$ and $A^6$ are —H, —CH$_3$,

CH$_2$OT or

$A^1$ and $A^6$ being the same or different, and at least one of which being the group:

in a lactam ring;

and where Q is —OT', —NHT' or a lactam linkage to $A^1$ or $A^6$;

the Q groups being the same or different, and at least one of which is involved in a lactam linkage;

and where T is the same or different and is chosen from —H, —C$_p$H$_{2p+1}$ or a metal ion, T' is —H or —COC$_p$H$_{2p+1}$, and p is an integer of from 1 to 22;

provided that:

where any of the Q groups is —OT' or —NHT', then that group or groups can be of either stereochemical configuration with respect to the plane of the ring; and
(ii) a cosmetically acceptable vehicle for the chemical inhibitor;
the total amount of chemical inhibitor present in the composition being sufficient to increase hair growth in the rat, when said composition is applied topically thereto over a period of no more than 3 months, by at least 10% more than that obtainable using a control composition from which the said inhibitors have been omitted in accordance with the Rat Hair Growth Test.

DISCLOSURE OF THE INVENTION

THE CHEMICAL INHIBITOR OF GLYCOSIDASE ACTIVITY

As has already been stated, a "chemical inhibitor" is a substance which is not only physiologically suitable and safe for topical application to skin, but which is capable of inhibiting glycosidase activity.

The chemical inhibitor of glycosidase activity is chosen from lactams having the structure:

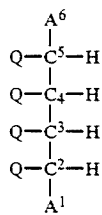  (1)

where $A^1$ and $A^6$ are —H, —CH$_3$,

—CH$_2$OT or

$A^1$ and $A^6$ being the same or different, and at least one of which being the group:

in a lactam ring;
and where Q is —OT', —NHT' or a lactam linkage to $A^1$ or $A^6$;
the Q groups being the same or different, and at least one of which is involved in a lactam linkage;
and where T is the same or different and is chosen form —H, —C$_p$H$_{2p+1}$ or a metal ion,
T' is —H or —COC$_p$H$_{2p+1}$, and
p is an integer of from 1 to 22;
provided that:
where any of the Q groups is —OT' or —NHT',
then that group or groups can be of either stereochemical configuration with respect to the plane of the ring.

A particular preferred example of the lactams derived from the above generic structure (1) is D-glucaro-1,5-lactam, an inhibitor of β-glucuronidase activity, having the structure (2)

Further examples of lactams include the following:
L-Galactono-1,4-lactam, an inhibitor of β-galactosidase and β-N-acetylhexosaminidase activity, having the structure (3);
L-Arabino-1,5-lactam, an inhibitor of β-galactosidase activity, having this structure (4);
D-Fucono-1,5-lactam, an inhibitor of β-galactosidase activity, having the structure (5);
D-Glucaro-1,4-lactam, an inhibitor of β-glucuronidase and α-L-iduronidase activity, having the structure (6):
D-Glucurono-6,3-lactam, an inhibitor of β-glucuronidase activity, having the structure (7);
1,2,5-tri-O-acetyl-D-glucurono-6,3-lactam an inhibitor of β-glucuronidase and α-L-iduronidase activity having the structure (8);
2-Acetamido-2-deoxyglucono-1,5-lactam, an inhibitor of β-N-acetylhexosaminidase, having the structure (9);
2-Acetamido-2-deoxygalactono-1,5-lactam, an inhibitor of β-N-acetylehexosaminidase, having the structure (10);
D-Glucaro-1,4:6,3-dilactam, an inhibitor of and βglucuronidase and α-L-iduronidase activity, having the structure (11);
L-Idaro-1,5-lactam, and inhibitor of α-L-iduronidase activity, having the structure (12);
Preferred examples of esterified forms of aldonolactams which give a more substained inhibitory effect are:
2,3,5-Tri-O-acetyl-D-glucaro-1,4-lactam, an inhibitor of β-glucuronidase and α-L-iduronidase activity, having the structure (13);
2,5-Di-O-acetyl-D-Glucaro-1,4:6,3-dilactam, an inhibitor of β-glucuronidase and α-L-iduronidase activity, having the structure (14);
D-Glucaro-1,5-lactam methyl ester, an inhibitor of β-glucuronidase activity, having the structure (15); and
2-Propionoamido-2-deoxygluraro-1,5-lactam, an inhibitor of β-glucuronidase acitivity, having the structure (16).

Mixtures comprising two or more of the chemical inhibitors can be employed in the composition according to the invention.

The total amount of chemical inhibitor present in the composition according to the invention is sufficient to increase hair growth in the rat, the model selected for this test, when said composition is applied topically thereto by at least 10% more than that obtainable using a control composition from which the said inhibitor has been omitted.

Preferably, the amount of chemical inhibitor should be sufficient to increase hair growth in the rat by at least 20%, more preferably by at least 30%, most preferably by at least 40% and ideally by at least 50%.

The sufficient amount will depend on the effectiveness of a chemical inhibitor, some being more effective than others, but in general, an amount of from 0.0001 to 99%, preferably from 0.1 to 20% by weight of the composition will provide an adequate dose to the skin after topical application.

The Vehicle

The composition according to the invention also comprises a solid, semi-solid or liquid cosmetically and/or physiologically acceptable vehicle, to enable the chemical inhibitor to be conveyed to the skin at an appropriate dilution The nature of the vehicle will depend upon the method chosen for topical administration of the composition. The vehicle can itself be inert or it can possess physiological or pharmaceutical benefits of its own.

It should be explained that vehicles are substances which can act as diluents, dispersants, or solvents for the chemical inhibitor which therefore ensure that it can be applied to and distributed evenly over the hair and/or scalp at an appropriate concentration. The vehicle is preferably one which can aid penetration of the inhibitors into the skin to reach the immediate environment of the hair follicle. Compositions according to this invention can include water as a vehicle, and/or at least one cosmetically acceptable vehicle other than water.

Vehicles other than water that can be used in compositions according to the invention can include liquids or solids as emollients, solvents, humectants, thickeners and powders. Examples of each of these types of vehicles, which can be used singly or as mixtures of one or more vehicles, are as follows:

Emollients, such as stearyl alcohol, glyceryl monoricinoleate, glyceryl monostearate, propane-1,2-diol, butane-1,3-diol, mink oil, cetyl alcohol, ispropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, dimethylpolysiloxane, di-n-butyl sebacate, isopropyl myristate, isopropyl palmitate, isopropyl stearate, butyl stearate, polythylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate;

Propellants, such as trichlorofluoromethane, dichlorodifluoromethane, dichlorotetrafluoroethane, monochlorodifluoromethane, trichlorotrifluoroethane, propane, butane, isobutane, dimethyl ether, carbon dioxide, nitrous oxide;

Solvents, such as ethyl alcohol, methylene chloride, isopropanol, acetone, castor oil, ethylene glycol monoethyl ether, diethylene glycol monobutyl ether, diethylene glycol monoethyl ether, dimethyl sulphoxide, dimethyl formamide, tetrahydrofuran;

Humectants, such as glycerin, sorbitol, sodium 2-pyrrolidone-5-carboxylate, soluble collagen, dibutyl phthalate, gelatin;

Powders, such as chalk, talc, fullers earth, kaolin, starch, gums, colloidal silicon dioxide, sodium polyacrylate, tetra alkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, ethylene glycol monostearate.

Activity Enhancer

The composition according to the invention also preferably comprises a means for enhancing the activity of the chemical inhibitor, as herein defined, to aid its penetration into and/or through the skin, or otherwise to enhance its benefits in increasing hair growth.

The activity enhancer can be chosen from a wide variety of molecules, in addition to some of the vehicles as hereinbefore described, which can function in different ways to enhance the hair growth effects of the chemical inhibitor. Particular classes of activity enhancers include other hair growth stimulants, penetration enhancers and cationic polymers, whose presence can further improve the delivery of the chemical inhibitor through the stratum corneum to its site of action in the immediate environment of the hair follicle.

Some activity enhancers can also function as vehicles for the chemical inhibitor.

The means for enhancing the activity of the chemical inhibitor can also take the form of an iontophoretic device as will be explained later. This and other means for enhancing the activity of said chemical inhibitors are now disclosed in greater detail.

(a) Other Hair Growth Stimulants

Examples of other substances which themselves possess the ability to stimulate or increase hair growth include, for example;
Benzalkonium chloride
Benzethonium chloride
Phenol
Estradiol
Diphenhydramine hydrochloride
Chlorpheniramine maleate
Chlorophyllin derivatives
Cholesterol
Salicylic acid
Cystine
Red pepper tincture
Benzyl nicotinate
dl-Menthol
Peppermint oil
Calcium pantothenate
Panthenol
Castor oil
Hinokitiol
Prednisolone
Resorcinol Further substances which themselves possess the ability to increase the rate of terminal hair growth include:
(i) α-1,4 esterified disaccharides described by Choay S. A. in EP-A-O No. 064 012, having the structure (50):

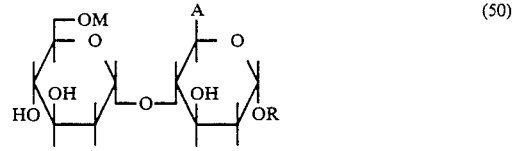
(50)

where
Z represents a functional nitrogen group, such as an azide or a group having the structure —NHB, in which B represents —H or a functional group such as acetyl or sulphate as a salt with an organic or mineral cation;

M represents —H or $SO_3M_1$, where $M_1$ is an organic or metallic cation, particularly an alkali metal; or an acetyl group;

R represents a $C_1$ to $C_4$ alkyl radical, especially methyl; or an aryl radical;

A represents a functional group such as an acid or —$COOR_1$, where $R_1$ represents —H or a $C_1$ to $C_4$ alkyl radical, especially methyl; or a metal, especially an alkali metal;

(ii) esterified oligosaccharides as described by Unilever in EP-A-O No. 211 610, including at least one esterified disaccharide unit consisting of a uronic acid residue having the structure (51):

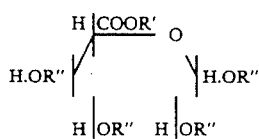
(51)

and a hexosamine residue having the structure (52):

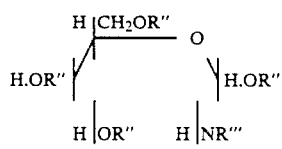
(52)

where
R' is —H, $C_3$ to $C_{10}$ alkyl or

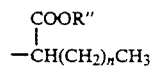

R" is —H, $C_1$ to $C_4$ alkyl, —$CO(CH_2)_mCH_3$, —$SO_3M'$,

R'" is —H, —$CO(CH_2)_mCH_3$, or —$SO_3M'$,

M' is —H, or a metallic or organic cation n is 0 or an integer of from 1 to 7, and m is 0 or the integer 1 or 2;

the groups designated R" being the same or different, one R" group from each pyranose ring structure being linked by a glycosidic linkage having the configuration $\alpha$-1,3, $\alpha$-1,4, $\beta$-1,3 or $\beta$-1,4; and the —COOR', —$CH_2OR"$ and —OR" groups being of either configuration with respect to the pyranose rings;

(iii) Minoxidil and its derivatives, as described by The Upjohn Co in GB No. 1 167 735, (iv) Minoxidil glucuronides, as described by Unilever in EP-O No. 242 967, (v) Minoxidil sulphates, as described by The Upjohn Co. in WO 86/04231.

(vi) Direct proteoglycanase inhibitors, such as 1,10-phenanthroline.

(vii) Glycosaminoglycanase inhibitors, such as aldonolactones and esterified aldonolactones having the structure (53):

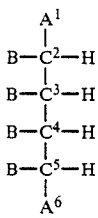
(53)

where $A^1$ and $A^6$ are —H, —$CH_3$,

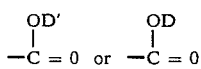

B is OD" or a lactone linkage to position 1 or 6, or —$NHCOCH_3$ and where D is —H or $C_2$ to $C_8$ alkyl, D' is the remainder of the molecule joined through another C atom at positions 2 to 5 to form a lactone, D" is —H or $C_2$ (i.e. acetyl) to $C_4$ acyl of either configuration with respect to the backbone of this molecule;

preferred examples of which include:
L-Galactono-1,4-lactone
L-Arabino-1,5-lactone
D-Fucono-1,5-lactone
D-Glucaro-1,4-lactone
D-Glucurono-6,3-lactone
Galactaric acid lactone
2-Acetamido-2-deoxygluconolactone
2-Acetamido-2-deoxygalactono-lactone
D-Glucaro-1,4:6,3-dilactone
L-Idaro-1,4-lactone
2,3,5-Tri-O-acetyl-D-glucaro-1,4-lactone
2,5-Di-O-acetyl-D-glucaro-1,4:6,3-dilactone (viii) Glycosaminoglycanase inhibitors, such as monosaccharides and esterified monosaccharides having the structure (54):

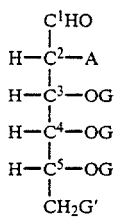
(54)

where A is —OG or —$NHCOCH_3$

G is —H, —SOM", $C_2$ (ie acetyl) to $C_4$ acyl

G' is —H or —OG

M" is —H or a metal cation wherein the functional groups can be in either configuration with respect to the backbone of the above molecule;

preferred examples of which include:
N-Acetylglucosamine
N-Acetylgalactosamine
D-Galactosamine
D-Glucosamine-3-sulphate
N-Acetylmannosamine (ix) glycosaminoglycan chain cellular uptake inhibitors such as, hexuronic acid and esters thereof which may be represented by the generic structure (55):

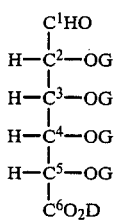

where
G is —H, —SOM'', $C_2$ (i.e. acetyl) to $C_4$ acyl;
D is —H or $C_2$ to $C_8$ alkyl
M'' is —H or a metal cation
wherein the functional groups can be in either configuration with respect to the backbone of the above molecule;
(x) chemical activators of protein kinase C enzymes chosen from diacylglycerols having the structure (56):

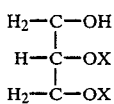

where X is the same or different, and is represented by the grouping:

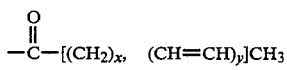

where x is 0, or an integer of from 1 to 28, and y is 0, or an integer of from 1 to 5;
the X groups being of either steriochemical configuration with respect to the carbon backbone of the glycerol molecule, and the double bonds being of either cis or trans configuration;
preferred examples of which include:
1,2-Dibutanoyl-rac-glycerol
1,2-Dihexanoyl-sn-glycerol
1,2-Dioctanoyl-rac-glycerol
1,2-Dioctanoyl-sn-glycerol
1,2-Didecanoyl-rac-glycerol
1-Oleoyl-2-acetyl-rac-glycerol
1-Oleoyl-2-acetyl-sn-glycerol
1-Stearoyl-2-arachidonoyl-sn-glycerol
1,2-Distearoyl-rac-glycerol
1,2-Dipentadecanoyl-sn-glycerol
1,2-dipentadecanoyl-rac-glycerol
1,2-Dipalmitoyl-rac-glycerol
1,2-Dipalmitoyl-sn-glycerol
1,2-Diseptadecanoyl-rac-glycerol
1,2-Dioleoyl-sn-glycerol
1,2-Dioleoyl-rac-glycerol
1,2-Diarachidonoyl-sn-glycerol
1,2-Dieicosanoyl-sn-glycerol
1,2-Didoeicosanoyl-rac-glycerol, and
1,2-Dioctaeicosanoyl-sn-glycerol.

(b) Penetration Enhancers

As has been stated earlier, the presence of a penetration enhancer can potentiate the benefit of the chemical inhibitor, by improving its delivery through the stratum corneum to its site of action in the immediate environment of the hair follicle close to the dermal papilla.

The penetration enhancer can accordingly function in a variety of ways. It can for example, improve the distribution of the chemical inhibitor on the skin surface or, it can increase its partition into the skin from the composition when applied topically, so aiding its passage to its site of action. Other mechanisms enhancing the benefit of the chemical inhibitor may also be involved.

Examples of penetration enhancers include:
2-methyl propan-2-ol
Propan-2-ol
Ethyl-2-hydroxypropanoate
Hexan-2,5-diol
POE(2) ethyl ether
Di(2-hydroxypropyl) ether
Pentan-2,4-diol
Acetone
POE(2) methyl ether
2-hydroxypropionic acid
2-hydroxyoctanoic acid
Propan-1-ol
1,4 Dioxane
Tetrahydrofuran
Butan-1,4-diol
Propylene glycol dipelargonate
Polyoxypropylene 15 stearyl ether
Octyl alcohol
POE ester of oleyl alcohol
Oleyl alcohol
Lauryl alcohol
Dioctyl adipate
Dicapryl adipate
Diisopropyl adipate
Diisopropyl sebacate
Dibutyl sebacate
Diethyl sebacate
Dimethyl sebacate
Dioctyl sebacate
Dibutyl suberate
Dioctyl azelate
Debenzyl sebacate
Dibutyl phthalate
Dibutyl azelate
Ethyl myristate
Dimethyl azelate
Butyl myristate
Dibutyl succinate
Didecyl phthalate
Decyl oleate
Ethyl caproate
Ethyl salicylate
Isopropyl palmitate
Ethyl laurate
2-ethyl-hexyl pelargonate
Isopropyl isostearate
Butyl laurate
Benzyl benzoate
Butyl benzoate
Hexyl laurate
Ethyl caprate
Ethyl caprylate
Butyl stearate
Benzyl salicylate
2-hydroxypropanoic acid
2-hyroxyoctanoic acid, Yet further penetration enhancers include esters of pyroglutamic acid having the structure (57):

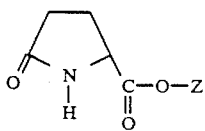 (57)

where
Z is $C_1$ to $C_{30}$ alkyl, or

and where Z' and Z" are the same or different and are each represented by H or the grouping (58):

$$[(CH_3)_u, (CH_2OH)_v, (CH_2)_w, (CH_3CH_2)_s, (CH=CH)_z]-$$ (58)

where
u is zero or 1
v is zero, or the integer 1 or 2,
w is zero, or an integer of from 1 to 21
s is zero, or an integer of from 1 to 4,
y is zero, or the integer 1 or 2,
z is zero, or an integer of from 1 to 22, and
$u+v+w+x+y+z$ is an integer of from 1 to 22;
provided that when the subgrouping (CH=CH) is present, then the total number of carbon atoms in said grouping is from 10 to 22.

Examples of suitable esters of pyroglutamic acid where Z in structure (57) is $C_1$ to $C_{30}$ alkyl are:
pyroglutamic acid methyl ester
pyroglutamic acid ethyl ester
pyroglutamic acid n-propyl ester
pyroglutamic acid n-butyl ester
pyroglutamic acid n-heptyl ester
pyroglutamic acid n-octyl ester
pyroglutamic acid n-nonyl ester
pyroglutamic acid n-decyl ester
pyroglutamic acid n-undecyl ester
pyroglutamic acid n-dodecyl ester
pyroglutamic acid n-tridecyl ester
pyroglutamic acid n-tetradcyl ester
pyroglutamic acid n-hexadecyl ester
pyroglutamic acid n-octadecyl ester
pyroglutamic acid n-eicosyl ester
pyroglutamic acid iso-propyl ester
pyroglutamic acid 2-methylhexyl ester
pyroglutamic acid 2-ethylhexyl ester
pyroglutamic acid 3,7-dimethyloctyl ester
pyroglutamic acid 2-hexyldecyl ester
pyroglutamic acid 2-octyldodecyl ester
pyroglutamic acid 2,4,4-trimetyl-1-pentane ester
pyroglutamic acid methyloctyl ester Particularly preferred esters of this group are those where Z in structure (1) is $C_1$ to $C_{14}$ alkyl, (linear or branched), especially $C_1$ to $C_6$ (linear or branched).

Further examples of preferred esters of pyroglutamic acid, where Z in structure (57) is

, are those where Z' and/or Z" having the structure shown for grouping (58), include straight and branched chain, saturated or unsaturated aliphatic groups having from 1 to 22 carbon atoms, such as the alkyl groups:
methyl
ethyl
propyl
iso-propyl
butyl
iso-butyl
n-valeryl
iso-valeryl
n-caproyl
n-heptyl
n-caprylyl
n-capryl
lauryl
myristyl
palmityl
stearyl, and
arachidyl
and the $C_{10-22}$ alkenyl groups:
linoleyl
linolenyl
γ-linolenyl
arachidonyl, and
columbinyl.

Further examples of the grouping (58) also include hydroxyalkyl groups having from 1 to 22 carbon atoms, such as:
hydroxymethyl
2-hydroxyethyl
2-hydroxy-n-propyl
3-hydroxy-n-propyl
2-hydroxy-n-butyl
3-hydroxy-n-butyl
4-hydroxy-n-butyl
5-hydroxy-n-valeryl
6-hydroxy-n-caproyl
2,3-dihydroxy-n-propyl
2,3-dihydroxy-n-butyl
12-hydroxystearyl.

It is to be understood that the above list is not exhaustive, there being many other examples of alkyl or substituted alkyl groups expressed by the above generic grouping (58).

Further specific examples of esters of pyroglutamic acid which are particularly suited to use as penetration enhancers are:
2-[pyroglutamoyloxy]-propionic acid
methyl-2-[pyroglutamoyloxy]-acetate
ethyl-2-[pyroglutamoyloxy]-n-propionate
ethyl-2-[pyroglutamoyloxy]-n-butyrate
ethyl-2-[pyroglutamoyloxy]-iso-butyrate
ethyl-2-[pyroglutamoyloxy]-n-valerate
ethyl-2-[pyroglutamoyloxy]-n-caproate
ethyl-2-[pyroglutamoyloxy]-n-heptylate
ethyl-2-[pyroglutamoyloxy]-n-caprylate
ethyl-2-[pyroglutamoyloxy]-n-pelargonate
ethyl-2-[pyroglutamoyloxy]-3-hydroxybutyrate
iso-propyl-2-[pyroglutamoyloxy]-n-propionate
iso-propyl-2-[pyroglutamoyloxy]-n-caprylate
n-propyl-2-[pyroglutamoyloxy]-n-propionate
n-propyl-2-[pyroglutamoyloxy]-n-caprylate
stearyl-2-[pyroglutamoyloxy]-n-propionate
12-hydroxystearyl-2-[pyroglutamoyloxy]-n-propionate
stearyl-2-[pyroglutamoyloxy]-n-stearate
palmityl-2-[pyroglutamoyloxy]-n-propionate linoleyl-2-[pyroglutamoyloxy]-n-propionate
linoleyl-2-[pyroglutamoyloxy]-n-caprylate
lauryl-2-[pyroglutamoyloxy]-n-caprylate
stearyl-2-[pyroglutamoyloxy]-n-caprylate
glyceryl mono(2-[pyroglutamoyloxy]-n-propionate)
glyceryl mono(2-[pyroglutamoyloxy]-n-caprylate), and
glyceryl di(2-[pyroglutamoyloxy]-n-propionate).

It is to be understood that the above lists of specific examples of esters of pyroglutamic acid are not exhaustive, there being many other examples expressed by the generic structure of these esters.

Further examples of penetration enhancers include:
Dimethyl sulphoxide
N,N-Dimethyl acetamide
N,N-Dimethyl formamide
2-Pyrrolidone
1-Methyl-2-pyrrolidone
5-Methyl-2-pyrrolidone
1,5-Dimethyl-2-pyrrolidone
1-Ethyl-2-pyrrolidone
Phosphine oxides
Sugar esters
Tetrahydrofurfural alcohol
Urea
Diethyl-m-toluamide, and
1-Dodecylazacyloheptan-2-one Further examples of penetration enhancers include surface active agents, preferred examples of which include:

(i)

Anionic surface active agents, such as metallic or alkanolamine salts of fatty acids for example sodium laurate and triethanolamine oleate;
alkyl benzene sulphonates, for example triethanolamine dodecyl benzene sulphonate;
alkyl sulphates, for example sodium lauryl sulphate;
alkyl ether sulphates, for example sodium lauryl ether sulphate [2 to 8 EO];
sulphosuccinate, for example sodium dioctyl sulphonsuccinate;
monoglyceride sulphates, for example sodium glyceryl monostearate monosulphate;
isethionates, for example sodium isethionate;
methyl taurides, for example Igepon T;
acylsarcosinates, for example sodium myristyl sarcosinate;
acyl peptides, for example Maypons and Lamepons;
acyl lactylates,
polyalkoxylated ether glycollates, for example trideceth-7 carboxylic acid;
phosphates, for example sodium dilauryl phosphate.

(ii)

Cationic surface active agents, such as amine salts, for example sapamin hydrochloride;
quarternary ammonium salts, for example Quaternium 5, Quaternium 31 and Quaternium 18;

(iii)

Amphoteric surface active agents, such as imidazol compounds, for example Miranol;
N-alkyl amino acids, such as sodium cocaminopropionate and asparagine derivatives;
betaines, for example cocoamidopropylbetaine (iv)

Nonionic surface active agents, such as fatty acid alkanolamides, for example oleic ethanolamide;
esters of polyalcohols, for example Span;
polyglycerol esters, for example that esterified with $C_{12-18}$ fatty acids and one or several OH groups;
polyalkoxylated derivatives, for example polyoxy:-polyoxyethylene stearate, and octylphenoxy polyethoxyethanol (TRITON X-100);
ethers, for example polyoxyethylene lauryl ether;
ester ethers, for example Tween;
amine oxides, for example coconut and dodecyl dimethyl amine oxides.

Mixtures of two or more of the above surface active agents can be employed in the composition according to the invention.

(c) cationic polymers chosen from:

Guar Hydroxypropyltrimonium chloride
Quaternium-19
Quaternium-23
Quaternium-40
Quaternium-57
Poly(dipropyldiallylammonium chloride)
Poly(methyl-β-propaniodiallylammonium chloride)
Poly(diallylpiperidinium chloride)
Poly(vinyl pyridinium chloride)
Quaternised poly (vinyl alcohol)
Quaternised poly (dimethylaminoethylmethacrylate); and
mixtures thereof.

The amount of vehicle in the composition, including water if present, should preferably be sufficient to carry at least a portion of a selected chemical inhibitor factor to the skin in an amount which is which is sufficient effectively to enhance hair growth. The amount of the vehicle can comprise the balance of the composition, particularly where little or no other ingredients are present in the composition. Accordingly, the vehicle or vehicles can comprise from 1 to 99.9999%, preferably from 50 to 99.5% by weight of the compositions.

The amount of activity enhancer, when employed in accordance with the invention, will normally be from 0.1 to 50%, preferably from 0.5 to 25% and most preferably from 0.5 to 10% by weight of the composition.

(d) Iontophoresis

A further means for enhancing the activity of chemical inhibitor following topical application is the use of iontophoretic. A preferred iotophoretic device for this purpose comprises a pad of absorbent material, such as a nonwoven sheet or sponge, impregnated with a solution of chemical inhibitor as herein defined, the pad carrying an electrode, for example in the form of a metallic sheet, through which an electric current can be passed, in order to enhance delivery of the chemical inhibitor to and through the epidermal layer of the skin.

Further preferred embodiments of the invention

Further preferred embodiments of the invention are those where the composition according to the invention comprises a second hair growth stimulant in addition to at least one lactam, as herein defined.

Particularly preferred mixtures include the following, where minoxidil can be employed in compositions according to the invention with a lactam.

Accordingly, preferred mixtures are:

Minoxidil and D-glucaro-1,5-lactam
Minoxidil and L-galactono-1,5-lactam
Minoxidil and L-idaro-1,5-lactam
Minoxidil and L-arabino-1,5-lactam
Minoxidil and 2,3,5-tri-O-acetyl-D-glucaro-1,5-lactam
Minoxidil and D-glucaro-1,5-lactam ethyl ester

Perfume

The composition according to the invention can also optionally comprise a perfume in an amount sufficient to make the composition acceptable to the consumer and pleasant to use. Usually, the perfume will form from 0.01 to 10% by weight of the composition.

Preservation of the Composition

The composition according to the invention is preferably preserved in such a manner that it will enjoy an extended shelf life following manufacture and prior to sale and use. Ideally the composition will have an indefinite shelf life.

It is accordingly apparent that the chemical inhibitor is likely to be prone to attack by bacteria, moulds and fungi and other microbial influences, particularly at pH values near neturality that characterise the preferred composition. The shelf-life of the composition can therefore be unacceptably short due to the biodegradation of the inhibitor unless steps are taken to preserve the composition.

In order to be preserved, the composition should preferably be free, or substantially free, from viable microbial contaminants that are capable of resulting in microbial spoilage of the composition, and/or biodegradation of the inhibitor prior to topical application of the composition to mammalian skin or hair. It is to be understood, however, that the invention is also concerned with compositions, as herein defined, which may contain viable but dormant microorganisms, such as bacterial spores, provided that the conditions of preservation do not result in substantial proliferation of the microorganisms prior to use of the composition.

Examples of methods that can be employed to achieve preservation of the composition, includes the following:

(i) Sterilisation

The composition according to the invention can be preserved by sterilisation to remove or kill substantially all viable microbial contaminants. This can be achieved for example by irradiation using a lethal dose of gamma rays, by heat sterilisation or by ultrafiltration using techniques that are well established in the pharmaceutical industry.

(ii) Extremes of pH value

The composition according to the invention can alternatively be preserved by adjusting its pH to a value that is either too low (e.g. pH <2) or too high (e.g. pH >12) to permit significant proliferation of microbial contaminants. The pH of the composition can accordingly be adjusted to desired high or low values by addition of an alkali or acid as a pH adjustant.

(iii) Chemical Preservative

The composition according to the invention can also be preserved by including in it a chemical preservative which functions to prevent the growth of or kill bacteria, fungi or other microorganisms.

Examples of chemical preservatives include ethanol, benzoic acid, sodium benzoate, sorbic acid, potassium sorbate, sodium propionate and the methyl, ethyl, propyl and butyl esters of p-hydroxybenzoic acid. The amount of chemical preservative that can be incorporated in the composition according to the invention will generally be from 0.05 to 5%, preferably from 0.1 to 2% by weight, the amount chosen being sufficient to arrest microbial proliferation.

(iv) Water activity depressants

The composition according to the invention can also be preserved by the inclusion of a water activity depressant such as glycerol, propylene glycol, sorbitol, sugars and salts, for examples alkali metal halides, sulphates and carboxylates When employing a water activity depressant, sufficient should be incorporated in the composition according to the invention to reduce the water activity ($a_w$) from 1 to <0.9, preferably to <0.85 and most preferably <0.8, the lowest of these values being that at which yeasts, moulds and fungi will not proliferate.

Other chemical inhibitor adjuncts

The composition according to the invention can also contain adjuncts other than those already mentioned, depending on the form of the intended product. It is, for example, possible to include antiseptics, antioxidants, emulsifiers, colouring agents, detergents and antiinflammatory agents which can improve the stability and consumer appeal of the composition. Examples of anti-inflammatory agents include steroidal (e.g., hydrocortisone and other corticosteroids) and non-steroidal (e.g., ibuprofen and its derivatives) compounds.

The composition according to the invention can also be employed as a vehicle for a wide variety of cosmetically or pharmaceutically active ingredients, particularly ingredients which have some beneficial effect other than the promotion of hair growth when applied to the skin.

Process

The invention also provides a process for the preparation of a composition suitable for topical application to mammalian skin or hair which comprises mixing a chemical inhibitor as herein defined, with a suitable vehicle to provide a composition according to the invention, in which the inhibitor forms from 0.0001 to 99% by weight of the composition.

Product Form and Container

The composition of the invention can be formulated as a liquid, for example as a lotion, shampoo, conditioner or milk or use in conjunction with an applicator such as a roll-ball applicator, or a spray device such as an aerosol can containing propellant, or a container fitted with a pump to dispense the liquid product.

When the composition is contained in a pressurised aerosol container, the propellant in providing an inert headspace within the container will aid in preserving the composition.

The composition of the invention can also be solid or semi-solid, for example a stick, cream or gel, for use in conjunction with a suitable applicator or simply a tube, bottle or lidded jar, or as a liquid-impregnated fabric, such as a tissue wipe.

The invention accordingly also provides a closed container containing the composition as herein defined.

Use of the Chemical Inhibitor for Inducing, Maintaining or Increasing Hair Growth The invention also provides for the use of a chemical inhibitor, as herein defined, for topical application to mammalian hair or skin particularly the scalp, for inducing, maintaining or increasing terminal hair growth, and/or converting vellus hair to growth as terminal hair.

The composition of the invention is accordingly primarily intended for topical application to the scalp of the human subject, particularly where the head is already bald or balding, in order to reduce or prevent the onset of baldness.

The invention also provides for the use of the inhibitor in the preparation of a therapeutic composition for treating baldness.

The amount of the composition and the frequency of application to the hair and/or scalp can vary widely, depending on personal needs, but it is suggested as an example that topical application of from 0.1 to 5 g daily containing from 0.00001 to 1 g of a selected chemical inhibitor over the period of at least six months will in most cases result in an improvement in hair growth.

EVALUATION OF EFFICACY OF CHEMICAL INHIBITORS USING THE RAT MODEL

The Rat Hair Growth Test

The effect of compounds on hair growth was assessed using male albino Wistar rats as an animal model. The rats were chosen from as few litters as possible and were each approximately 42 days of age at the start of the test. Each rat was housed individually to prevent licking.

In each comparison, 10 rats were used in each group and hair growth was assessed as follows:

A small patch of normal skin (4 cm×4 cm) on the upper back of each rat was clipped at the start and 0.3 ml of a hair growth stimulant composition (or a control) applied topically twice daily and once on Saturdays and Sundays to each clipped area. The concentration of test compound in the composition was 0.2 mg/ml.

Hair was clipped from the area of the patch twice weekly, collected and weighed at each time point over a standard period of 3 months, and cumulative hair weight calculated. From these data, it was possible to estimate the effect of a hair growth stimulant as a test compound on the amount and duration of hair growth during the experiment. A positive response, i.e. an increase of at least 10% by weight of hair after 3 months treatment, compared with a control indicates the potential of the test compound to prevent hair loss and/or reverse baldness in human subjects.

Accordingly, when the chemical inhibitors, as herein defined, are assessed either individually or in combination as test compounds by the Rat Hair Growth Test, an increase of at least 10% by weight of hair after 3 months treatment will be obtained. Usually, the 10% by weight minimum value will be attained well before the end of this 3 month period.

EXAMPLES

The invention is illustrated by the following examples, in each of which the lactam structure number is given in parenthesis.

Example 1

This Example illustrates a lotion according to the invention which is suitable for topical application to the scalp in order to promote hair growth.

| The lotion has the following formulation: | |
|---|---|
| | % w/w |
| L-Galactono-1,4-lactam (3) | 0.1 |
| ethanol | 99.995 |
| perfume | q.s. |

Example 2

This Example illustrates a hair tonic which is suitable for application to hair or scalp.

| The hair tonic has the following formulation: | |
|---|---|
| | % w/w |
| L-Arabino-1,5-lactam (4) | 0.8 |
| ethanol | 50 |
| water | 49 |
| perfume | q.s. |

Example 3

This Example also illustrates a lotion which is suitable for topical application to the scalp.

| The lotion has the following formulation: | |
|---|---|
| | % w/w |
| D-Fucono-1,5-lactam (5) | 1.5 |
| propan-2-ol | 10 |
| ethanol | 88.5 |
| perfume | q.s. |

Example 4

This example also illustrates a hair tonic which is suitable for application to hair or scalp.

| The hair tonic has the following formulation: | |
|---|---|
| | % w/w |
| D-Glucaro-1,5-lactam (2) | 0.2 |
| ethanol | 40 |
| water | 59.80 |
| perfume | q.s. |

Examples 5 to 8

The following formulations represent lotions which can be used topically in the treatment of bald or balding male or female heads.

| | % w/w | | | |
|---|---|---|---|---|
| | 5 | 6 | 7 | 8 |
| Hydroxyethyl cellulose | 0.4 | — | 0.4 | — |
| Absolute ethanol | 25 | 25 | 25 | 25 |
| Propane-1,2-diol | — | — | 38.4 | 38.4 |
| Butane-1,3-diol | 38.4 | 38.8 | — | — |
| Paramethyl benzoate | 0.2 | 0.2 | 0.2 | 0.2 |
| D-Glucaro-1,4:6,3-dilactam (11) | 5 | — | — | — |
| L-Idaro-1,5-lactam (12) | — | 1 | — | — |
| D-Glucurono-6,3-lactam (7) | — | — | 0.8 | — |

-continued

|  | % w/w | | | |
|---|---|---|---|---|
|  | 5 | 6 | 7 | 8 |
| Acylated glucurono lactam* | — | — | — | 0.6 |
| Perfume | 1 | 1 | 1 | 1 |
| Water | to 100 | 100 | 100 | 100 |

*1,2,5-tri-O-acetyl-D-glucurono-6,3-lactam (8)

Examples 9 to 12

The following formulations represent creams which can be used in the treatment of baldness.

|  | % w/w | | | |
|---|---|---|---|---|
|  | 9 | 10 | 11 | 12 |
| Cetyl alcohol polyoxyethylene (10) | 4 | 4 | 4 | 4 |
| Cetyl alcohol | 4 | 4 | 4 | 4 |
| Mineral oil | 4 | 2 | — | — |
| Paraffin wax | — | 2 | 4 | — |
| Partial glyceride of palmitic and stearic acids | — | — | — | 4 |
| N-Acetylglucosamine-lactam* | 2 | — | — | — |
| N-Acetylgalactosamino-lactam+ | — | — | — | 1 |
| L-Arabino-1,5-lactam (4) | — | — | 1.5 | — |
| D-Fucaro-1,5-lactam- (5) | — | 2 | — | — |
| Triethanolamine | 0.75 | 0.75 | 0.75 | 0.75 |
| Butane-1,3-diol | 3 | 3 | 3 | 3 |
| Xanthan gum | 0.3 | 0.3 | 0.3 | 0.3 |
| Preservative | 0.4 | 0.4 | 0.4 | 0.4 |
| Perfume | q.s. | q.s. | q.s. | q.s. |
| Water | to 100 | 100 | 100 | 100 |

*2-Acetamido-2-deoxyglucono-1,5-lactam (9)
+2-Acetamido-2-deoxygalactonolactam (10)

Example 13

This Example illustrates a water-in-oil high internal phase emulsion containing a glycosaminoglycanase inhibitor according to the invention.

The emulsion consisted of 10% by volume oily phase and 90% by weight aqueous phase.

The oily phase and the aqueous phase had the following constitution:

|  | % w/w |
|---|---|
| Oily phase | |
| Sorbitan monooleate | 20 |
| Quartenium-18 hectorite | 5 |
| Liquid paraffin | 75 |
| Aqueous phase | |
| D-glucaro-1,5-lactam ethyl ester* | 0.5 |
| Xanthan gum | 1 |
| Preservative | 0.3 |
| Perfume | q.s. |
| Sodium chloride (1% w/w solution) | to 100 |

*esterified (2)

The emulsion was prepared by taking 10 parts by volume of the oily phase and to it adding slowly with stirring 90 parts by volume of the aqueous phase.

The high internal phase water-in-oil emulsion so formed can be applied topically to the scalp, to improve hair growth and regrowth.

The following examples 14 to 18 illustrate shampoos for use in washing the hair and scalp, and for promoting hair growth on the scalp.

Example 14

| Example 14 | |
|---|---|
|  | % w/w |
| Sodium lauryl ether sulphate (2 EO) [21% AD] | 41.4 |
| Lauryl dimethylamino acetic acid betaine: [30% AD] | 4 |
| Coconut fatty acid diethanolamine | 1.5 |
| Oleyl triethoxy phosphate (BRIPHOS 03D) | 1 |
| Polyglycol-polyamine condensation resin (POLYQUART H) [50% active] | 1.5 |
| Preservative, colouring matter, salt | 0.58 |
| D-glucaro-1,5-lactam butyl ester* | 5 |
| Perfume | q.s. |
| Water | to 100 |

*esterified (2)

Example 15

| Example 15 | |
|---|---|
|  | % w/w |
| Sodium lauryl ether sulphate (2 EO) [100% AD] | 12 |
| POLYMER JR400 | 2.5 |
| BRIPHOS 03D | 2.5 |
| D-Glucaro-1,4:6,3-dilactam (11) | 4 |
| Magnesium Sulphate | 5 |
| Perfume | q.s. |
| Water | to 100 |

Example 16

| Example 16 | |
|---|---|
|  | % w/w |
| Monoethanolamine lauryl sulphate [100% AD] | 20 |
| JAGUAR C13S | 3 |
| BRIPHOS 03D | 1.7 |
| Coconut diethanolamide | 5 |
| D-Glucaro-1,4-lactam (6) | 1 |
| Zinc gluconate | 3 |
| Perfume | q.s. |
| Water | to 100 |
| pH adjusted to 6.5 | |

Example 17

| Example 17 | |
|---|---|
|  | % w/w |
| Sodium lauryl ether sulphate (3 EO) [100% AD] | 12 |
| JAGUAR C13S | 0.3 |
| BRIPHOS 03D | 1 |
| L-Idaro-1,5-lactam (12) | 2 |
| Sodium chloride | 4 |
| Perfume | q.s. |
| Water | to 100 |
| pH adjusted to 6.5 | |

Example 18

|  | % w/w |
|---|---|
| Sodium lauryl ether sulphate (2 EO) [100% AD] | 12 |
| POLYMER JR400 | 3 |
| BRIPHOS 03D | 1 |

-continued

|  | % w/w |
|---|---|
| Opacifier | 9 |
| L-Idaro-1,5-lactam propyl ester* | 5 |
| Perfume | q.s. |
| Water to | 100 |
| pH adjusted to 6.5 | |

*esterified (12)

Examples 19 to 24

The following Examples 19 to 24 illustrate powder compositions according to the invention which can be applied topically to the scalp.

|  | % w/w | | | | | |
|---|---|---|---|---|---|---|
|  | 19 | 20 | 21 | 22 | 23 | 24 |
| Chemically modified starch | 5 | — | 5 | — | 5 | — |
| Chemically modified cellulose | — | 5 | — | 5 | — | 5 |
| Boric acid | 10 | 10 | 10 | 10 | 10 | 10 |
| Zinc oxide | 5 | 5 | 5 | 5 | 5 | 5 |
| D-Glucaro-1,4-lactam (6) | 3 | 2 | 5 | 1 | — | — |
| Minoxidil glucuronide | 5 | 10 | 2 | 4 | 3 | 5 |
| D-Glucaro-1,4:6,3-dilactam (11) | — | — | — | 2 | 5 | 3 |
| Perfume | q.s. | q.s. | q.s. | q.s. | q.s. | q.s. |
| Chalk | 10 | 10 | 10 | 10 | 10 | 10 |
| Talc to | 100 | 100 | 100 | 100 | 100 | 100 |

Example 25

The following example illustrates a lotion according to the invention which can be applied topically to the scalp to prevent hair loss and stimulate hair regrowth.

|  | % w/w |
|---|---|
| D-Glucaro-1,5-lactam (2) | 7 |
| Minoxidil | 0.2 |
| ethanol | 16 |
| citric acid | 1.05 |
| water to | 100 |
| pH adjusted to 4.2 with sodium hydroxide | |

Examples 26 and 27

These examples illustrate hair tonics which are suitable for application to the hair and scalp.

| The hair tonics had the following formulation: | | |
|---|---|---|
|  | % w/w | |
|  | 26 | 27 |
| L-Galactaro-1,4-lactam (3) | 2 | — |
| Trilactam* | — | 3 |
| ethanol | 50 | 50 |
| water | 48 | 47 |
| perfume | q.s. | q.s. |

*2,3,5-Tri-O-acetyl-D-glucaro-1,4-lactam (13)

Example 28

This example illustrates a microgel which is suitable for topical application to hair or scalp.
The gel had the following formulation:

| The gel had the following formulation: | | |
|---|---|---|
|  |  | % w/w |
| A. | Polyoxyethylene (10) oleyl ether | 14.5 |
|  | Polyoxyethylene fatty glyceride | 14.5 |
|  | Light liquid petroleum | 13.7 |
|  | Propylene glycol | 7.6 |
|  | Sorbitol | 5.9 |
|  | Dilactam* | 4 |
| B. | Perfume | q.s. |
| C. | Water to | 100 |

*2,5-Di-O-acetyl-D-glucaro-1,4:6,3-dilactam (14)

This microgel was prepared by heating part A to 90° C. and part C to 95° and then adding part C to part A with stirring. Part B was then added at 70° C. and the final mixture cooled and poured into jars at 55° C. to 60° C. On further cooling, a gel was formed.

Examples 29 to 31

These examples illustrate shampoos which are suitable for topical application to hair in order to cleanse it, at the same time delivering chemical inhibitors to the scalp to enhance hair growth or regrowth.

| The shampoo had the following formulation: | | | |
|---|---|---|---|
|  | 29 | 30 | 31 |
| Triethanolamine lauryl sulphate | 16.8 | 18.0 | 16.8 |
| Coconut diethanolamide | 3.0 | — | 1.0 |
| Hydroxypropylmethyl-cellulose (a) | 0.25 | 0.1 | 0.3 |
| Corn syrup (80% solids) (b) | 20.5 | 40.0 | 21.0 |
| Dimethylpolysiloxane (c) | 1.0 | 1.0 | — |
| Volatile silicone (d) | — | — | 1.0 |
| Cationic cellulose (e) | 0.5 | — | 0.5 |
| Ethyl alcohol (SDA 40) | 9.0 | 10.0 | 10.0 |
| Vinyl carboxy polymer (f) | 0.75 | 0.3 | 0.75 |
| D-Glucaro-1,5-lactam (2) | 1 | — | — |
| D-Galactono-1,4-lactam (3) | — | 2 | — |
| D-Glucaro-1,4-lactam (6) | — | — | 5 |
| Minoxidil | 0.5 | 0.5 | 0.5 |
| Perfume, colour, preservative | q.s. | q.s. | q.s. |
| Water to | 100 | 100 | 100 |
| Acid or base to pH: | 6.5 | 6.5 | 6.5 |

(a) - Methocel E4M (Dow Chemical)
(b) - 42 Dextrose equivalent (Staley 1300)
(c) - 60,000 centistokes (Viscasil, GEC)
(d) - Dow Corning 344
(e) - Polymer JR 400
(f) - Carbopol 941 (BF Goodrich)

Examples 32 to 35

The following formulations represent lotions which an be used topically in the treatment of bald or balding ale or female heads.

|  | % w/w | | | |
|---|---|---|---|---|
|  | 32 | 33 | 34 | 35 |
| Hydroxyethyl cellulose | 0.4 | — | 0.4 | — |
| Absolute ethanol | 25 | 25 | 25 | 25 |
| Propane-1,2-diol | — | — | 38.4 | 38.4 |
| Butane-1,3-diol | 38.4 | 38.8 | — | — |
| Paramethyl benzoate | 0.2 | 0.2 | 0.2 | 0.2 |
| D-Glucaro-1,5 lactam methyl ether (15) | 5 | — | — | — |
| 2-Propionoamido-2-deoxy glucaro-1,5-lactam (16) | — | 1 | — | — |
| D-Glucaro-1,5-lactam ethyl ester* | — | — | 2 | — |
| D-Glucaro-1,5-lactam propyl ester* | — | — | — | 4 |
| Minoxidil | 0.2 | 0.2 | 0.2 | 0.2 |

-continued

| | % w/w | | | |
|---|---|---|---|---|
| | 32 | 33 | 34 | 35 |
| Perfume | 1 | 1 | 1 | 1 |
| Water to | 100 | 100 | 100 | 100 |

*esterified (2)

Example 36

This Example also illustrates a lotion which is suitable for topical application to the scalp.

| The lotion has the following formulation: | |
|---|---|
| | % w/w |
| D-Glucurono-6,3-lactam (7) | 1.5 |
| Diisopropyl sebacate | 10 |
| ethanol | 88.5 |
| perfume | q.s |

Example 37

This Example also illustrates a hair tonic which is suitable for application to hair or scalp.

| The hair tonic has the following formulation: | |
|---|---|
| | % w/w |
| D-Glucurono-6,3-lactam (7) | 0.2 |
| Pyroglutamic acid ethyl ester | 10 |
| ethanol | 40 |
| water | 49.80 |
| perfume | q.s. |

I claim:

1. A process for the synthesis of a lactam which comprises the steps of treating an esterified deoxyamino uronic acid with a base to yield a lactam and recovering same, said lactam having the structure:

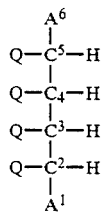
(1)

where $A^1$ and $A^6$ are $-H$, $-CH_3$,

$-CH_2OT$ or

$A^1$ and $A^6$ being the same or different, and at least one of which being the group:

in a lactam ring;
and where Q is $-OT'$, $-NHT'$ or a lactam linkage to $A^1$ or $A^6$;
the Q groups being the same or different, and at least one of which is involved in a lactam linkage;
and where T is the same or different and is chosen from $-H$, $-C_pH_{2p+1}$ or a cation,
T' is $-H$ or $-COC_pH_{2p+1}$, and
p is an integer of from 1 to 22;
provided that:
where any of the Q groups is $-OT'$ or $-NHCOT'$,
then that group or groups can be of either stereochemical configuration with respect to the plane of the ring,
provided also that where the lactam has the structure:

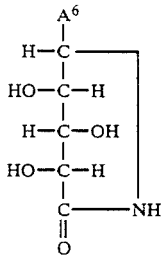
(1a)

and when $A^6$ is

and T is $-C_pH_{2p+1}$, then p is an integer of from 5 to 22.

2. A process according to claim 1 wherein the lactam selected is from the group consisting of:
L-Galactono-1,4-lactam,
L-Arabino-1,5-lactam,
D-Fucono-1,5-lactam,
D-Glucaro-1,4-lactam,
D-Glucurono-6,3-lactam,
1,2,5-Tri-O-acetyl-D-glucurono-6,3-lactam,
2-Acetamido-2-deoxyglucono-1,5-lactam,
D-Glucaro-1,4:6,3-dilactam,
L-Idaro-1,5-lactam, and
mixtures thereof.

3. A process according to claim 1 wherein the lactam is selected from the group consisting of:
2,3,5-Tri-O-acetyl-D-glucaro-1,4-lactam,
2,5-Di-O-acetyl-D-Glucaro-1,4:6,3-dilactam,
D-Glucaro-1,5-lactam methyl ester,
2-Propionoamide-2-deoxyglucaro-1,5-lactam, and
mixtures thereof.

4. A composition suitable for topical application to mammalian skin or hair for inducing, maintaining or increasing hair growth which comprises:
(i) a chemical inhibitor of glycosidase activity chosen from lactams having the structure:

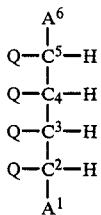

(1)

where $A^1$ and $A^6$ are —H, —$CH_3$,

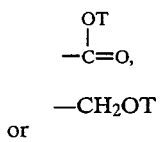

—$CH_2OT$ or

$A^1$ and $A^6$ being the same or different, and at least one of which being the group:

in a lactam ring;
and where Q is —OT', —NHT' or a lactam linkage to $A^1$ or $A^6$;
the Q groups being the same or different, and at least one of which is involved in a lactam linkage;
and where T is the same or different and is chosen from —H, —$C_pH_{2p+1}$ or a cation,
T' is —H or —$COC_pH_{2p+1}$, and
p is an integer of from 1 to 22;
provided that:
where any of the Q groups is —OT' or —NHT', then that group or groups can be of either stereochemical configuration with respect to the plane of the ring; and
(ii) a cosmetically acceptable vehicle for the chemical inhibitor; and
wherein the total amount of chemical inhibitor present in the composition is sufficient to increase hair growth in the rat, when said composition is applied topically thereto over a period of no more than 3 months, by at least 10% more than that obtainable using a control composition from which said inhibitor has been omitted, in accordance with the Rat Hair Growth Test, said lactam being selected from the group consisting of:
L-Galactono-1,4-lactam,
L-Arabino-1,5-lactam,
D-Fucono-1,5-lactam,
D-Glucaro-1,4-lactam,
D-Glucurono-6,3-lactam,
1,2,5-Tri-O-acetyl-D-glucurono-6,3-lactam,
2-Acetamido-2-deoxyglucono-1,5-lactam,
2-Acetamido-2-deoxygalactono-1,5-lactam,
D-Glucaro-1,4:6,3-dilactam,
L-Idaro-1,5-lactam.
2,3,5,Tri-O-acetyl-D-glucaro-1,4-lactam,
2,5-Di-O-acetyl-D-Glucaro-1,4:6,3-dilactam,
D-Glucaro-1,5-lactam methyl ester,
2-Propionoamide-2-deoxyglucaro-1,5-lactam, and
mixtures thereof.

5. The composition of claim 4, wherein in the total amount of chemical inhibitor present in the composition is sufficient to increase hair growth in the rat by at least 20% more than that obtainable using a control composition from which the chemical inhibitor has been omitted, in accordance with the Rat Hair Growth Test.

6. The composition of claim 4, wherein which the chemical inhibitor forms from 0.0001 to 99% by weight of the composition.

7. The composition of claim 4, which additionally comprises a means for enhancing the activity of said chemical inhibitor following topical application to the skin.

8. The composition of claim 7, wherein the means for enhancing the activity of said growth factor is another hair growth stimulant selected from the group consisting of:
(i) α-1,4 esterified disaccharides having the structure (50);
(ii) esterified oligosaccharides including at least one esterified disaccharide unit consisting of uronic acid residue having the structure (51) and a hexosamine residue having the structure (52);
(iii) minoxidil and its derivatives;
(iv) minoxidil glucuronide;
(v) minoxidil sulphates;
(vi) direct proteoglycanase inhibitors;
(vii) glycosaminoglycanase inhibitors;
(viii) glycosaminoglycan chain cellular uptake inhibitors;
(ix) chemical activators of protein kinase C; and
(x) mixtures thereof.

9. The composition of claim 8, wherein the hair growth stimulant is minoxidil.

10. The composition of claim 8, wherein the glycosaminoglycanase inhibitor is an aldonolactone or an esterified aldonolactone having the structure (53).

11. The composition of claim 8, wherein the glycosaminoglycanase inhibitor is a monosaccharide or esterified monosaccharide having the structure (54).

12. The composition of claim 8, wherein the chemical activator of protein kinase C is a diacylglycerol having the structure (56).

13. The composition of claim 7, wherein the means for enhancing the activity of said growth factor is a penetration enhancer.

14. The composition of claim 13, wherein the penetration enhancer is selected from the group consisting of:
1-dodecylazacycloheptan-2-one
dibutyl sebacate
2-hydroxyoctanoic acid
esters of pyroglutamic acid having the structure (10)
and mixture thereof.

15. The composition of claim 13, wherein the penetration enhancer is a surface active agents.

16. The composition of claim 7, wherein the means for enhancing the activity of said growth factor is a cationic polymer.

17. The composition of claim 7, wherein the means for enhancing the activity of said growth factor is an iontophoretic device.

18. A method of converting vellus hair to growth as terminal hair which comprises the step of applying to the scalp in the region of vellus hair an effective amount of the composition according to claim 4.

19. A method for increasing the rate of terminal hair growth which comprises the step of applying to the scalp in the region of terminal hair an effective amount of the composition according to claim 4.

* * * * *